United States Patent [19]

Whittaker

[11] Patent Number: 5,024,324
[45] Date of Patent: Jun. 18, 1991

[54] SINGLE USE DENTAL FLOSS SPINDLE AND METHOD

[76] Inventor: Dale Whittaker, 1329 Quail Run Cir., Bentonville, Ark. 72712

[21] Appl. No.: 577,146

[22] Filed: Sep. 4, 1990

Related U.S. Application Data

[63] Continuation-in-part of Ser. No. 461,846, Jan. 8, 1990, Pat. No. 4,972,946, and a continuation-in-part of Ser. No. 476,020, Feb. 6, 1990, Pat. No. Des. 312,710.

[51] Int. Cl.$^5$ .................. A45D 40/24; A65D 85/00
[52] U.S. Cl. .................. 206/63.5; 53/425; 53/430; 132/324; 206/388
[58] Field of Search .......... 53/399, 430, 425; 132/323–327; 206/49, 63.3, 63.5, 368, 388, 389, 408, 820

[56] References Cited

U.S. PATENT DOCUMENTS

| | | | |
|---|---|---|---|
| 250,430 | 12/1881 | Bertsche et al. | 206/338 |
| 2,083,398 | 6/1937 | Rohland | 206/388 |
| 2,176,308 | 10/1939 | Larkin | 206/63.5 |
| 3,357,549 | 12/1967 | Staiti | 206/63.5 |
| 4,161,075 | 7/1979 | Eubanks et al. | 206/388 |
| 4,211,330 | 7/1980 | Strock | 206/63.5 |
| 4,258,843 | 3/1981 | Wymer | 206/63.3 |
| 4,530,129 | 7/1985 | Labick et al. | 206/63.5 |
| 4,579,221 | 4/1986 | Corella | 206/63.5 |
| 4,588,089 | 5/1986 | Yanz, Jr. et al. | 206/63.5 |
| 4,836,227 | 6/1989 | Charatan | 132/324 |
| 4,852,728 | 8/1989 | Court | 206/63.5 |

FOREIGN PATENT DOCUMENTS 0008363 of 1907 United Kingdom ............... 206/389

*Primary Examiner*—Jimmy G. Foster
*Attorney, Agent, or Firm*—Robert R. Keegan

[57] ABSTRACT

There is disclosed a variety of single-use dental floss spindles and the process for their production from an elongated strip of semi-rigid sheet material such as paperboard, plastic or a combination thereof, such spindles being generally rectangular, preferably about two inches long by three-quarters inch wide or less, and having wound lengthwise thereon about two feet of dental floss. The spindles are preferably provided with arcuate or straight sided indentations on the ends thereof to better retain the dental floss. Other indentations or openings along the mid-section of the spindles optionally are provided for ease of use or facility of manufacture. Preferably the beginning and finishing ends of floss are secured near opposite edges of a face of the spindles and are retained by a strip of self-adhesive tape or the like, the ends and tape having been severed along with the spindle sheet as one of the last steps of the process of products carried out by hand or by machine or some combination thereof. The process includes the steps of winding six or more turns of dental floss at one winding position marked by indentations, then leading dental floss to the next indentations and winding a similar number of turns at this winding position, with this step being repeated many times. Following the completion of several windings a self-adhesive tape is laid down over the sheet and finished windings; the elongated strip is cut into individual spindles, and, optionally, the spindles are sealed in plastic envelopes with the spindle and interior of the package sterilized by heat, radiation, or otherwise.

20 Claims, 2 Drawing Sheets

SINGLE USE DENTAL FLOSS SPINDLE AND METHOD

This application is a continuation-in-part of the inventor's prior copending applications Ser. No. 07/461,846 filed Jan. 8, 1990, U.S. Pat. No. 4,972,946, and application Ser. No. 07/476,020, filed Feb. 6, 1990, Pat. No. Des. 312710.

The present application relates to spindles or holders for dental floss particularly adapted to provide a convenient length of one to three feet of dental floss for a single use as opposed to the bulky container of some tens of yards of floss suitable to be kept in the medicine cabinet. Preferably the single use dental floss carrier will be sealed in an air-tight envelope and sterilized or otherwise sanitized for use in flossing the teeth upon opening the envelope.

A single use dental floss package of this general character is shown in the above application Ser. No. 07/476,020 now Pat. No. Des. 312710. The present invention particularly relates to the process for rapidly and economically producing large numbers of floss wound spindles or carriers and the product produced by the novel process.

A prior art bulky container with a long multi-use strand of dental floss therein is disclosed in U.S. Pat. No. 4,019,522 to Elbreeder granted Apr. 26, 1977 (Cl. 132/90). Single use dental floss packages and methods for producing them are known as exemplified by U.S. Pat. No. 4,852,728 to Court granted Aug. 1, 1989 (Cl. 206/63.5); U.S. Pat. No. 4,693,365 to Corella granted Sept. 15, 1987 (Cl. 206/63.3); and U.S. Pat. No. 4,105,120 to Bradberry granted Aug. 8, 1978 (Cl. 206/581). Such prior dental floss packages do not employ a small spindle wound with an appropriate length of dental floss as described and claimed herein, but rather show loose coils of dental floss or other arrangements. It follows that the above patents do not disclose a method for producing single use dental floss spindles of the kind disclosed herein.

There are other prior patents on products and processes which may be deemed relevant in that they show cards or spindles wound with strands of sewing thread or the like. Typical of such patents are U.S. Pat. No. 897,173 to R. W. Strassberger (Cl. 206/388xr) granted Aug. 25, 1908; U.S. Pat. No. 250,430 to A. Engisch, et al., (Cl. 206/388) granted Dec. 6, 1881; and U.S. Pat. No. 130,672 to H. Sutro granted Aug. 20, 1872.

In addition to the fact that the above three patent disclosures show articles which are not intended for dental floss holders and are generally unsuited for use as a dental floss spindle, they are otherwise dissimilar to the product and process disclosed and claimed herein. One element in particular that is absent from all of the above references and any prior art known to the inventor is the provision of a self-adhesive tape strip or other means for detachably securing the ends of the dental floss to the spindle. Also, to the extent that processes for producing the card-spindles are disclosed, such processes differ from the processes described herein.

The present invention provides various forms of single use dental floss spindles produced by a specified process from an elongated strip of paperboard, plastic or the like. The finished spindles are preferably rectangular in shape no larger than about two inches long by about one inch wide and have wound lengthwise thereon a length of dental floss about eighteen inches in the usual case. In a preferred form indentations on the ends of the spindle serve to better retain the dental floss and to mark the winding position on the elongated strip before it is cut. The indentations may be rectilinear or arcuate. Other indentations or openings along the midsections of the spindles may be provided for ease of use or efficiency of production.

In a preferred embodiment the beginning and finishing ends of floss are secured near the centers of the long edges of the spindles and are removably retained by a strip of self-adhesive tape or a small drop of adhesive material. It will be understood that the above mentioned long edges of the spindles are not defined until the elongated strip has been wound with several windings of floss and the floss end securing means has been applied, at which time floss and tape is severed with a single cut to separate one spindle from the remaining uncut spindles. The process of production may be carried out by hand, by machine, or some combination thereof. More specifically the process includes the steps of winding six or more turns of dental floss at one winding position, which is preferably marked by indentations, then leading dental floss to the next indentation and winding a similar number of turns at this winding position, with such steps being repeated many times. Following the completion of several windings, the self-adhesive tape or other floss end securing means is laid down on the sheet and the finished windings. Thereafter, the elongated strip is cut into individual spindles. Subsequently, the spindles may be sealed in plastic envelopes in a conventional manner, and the spindle and interior of the package may be sterilized by heat, radiation, or other conventional means.

In addition to providing the features and advantages described above, it is an object of the present invention to provide a small individual-use dental floss package wherein the dental floss is wound in six turns or more on a card-like spindle with the beginning and finishing ends of the floss held against the spindle card, the spindle and floss being sealed in a small bag or envelope which may be transparent and which is easily torn or otherwise opened in some conventional manner.

It is another object of the present invention to provide a small spindle having a single use length of dental floss wound thereon, such product being produced by winding at least six turns of dental floss at one winding position on an elongated semi-rigid strip of sheet material at a position marked by indentations then leading dental floss to the next indentations and winding a similar number of turns, with this step being repeated many times; and, following the completion of several windings, securing the floss between windings to the strip by a self-adhesive tape or other means and cutting the strip into individual spindles with transverse cuts of the strip between successive winding positions.

It is still another object of the present invention to provide single use dental floss spindles sealed in packages with sterilized interiors wherein the spindles are produced by winding dental floss on an elongated strip of sheet material at spaced apart winding positions and thereafter cutting the strip and floss to produce a single use dental floss spindle as described above.

It is yet another object of the present invention to provide a process for producing single use dental floss spindles or the like including steps of winding six or more turns of dental floss at one winding position marked by indentations then leading dental floss to the next indentations and winding it the same number of turns at each of these winding positions, with this step being repeated many times, wherein, after the completion of several windings, a self-adhesive tape or other suitable medium is laid down on the sheet to secure the dental floss to the sheet between the windings, and wherein the elongated strip is thereafter cut into individual spindles which are wound with a single use length of dental floss with the ends detachably secured to the sheet material of the spindle.

Other objects and advantages of the invention will be apparent from consideration of the following description in conjunction with the appended drawings in which.

Figure 1:
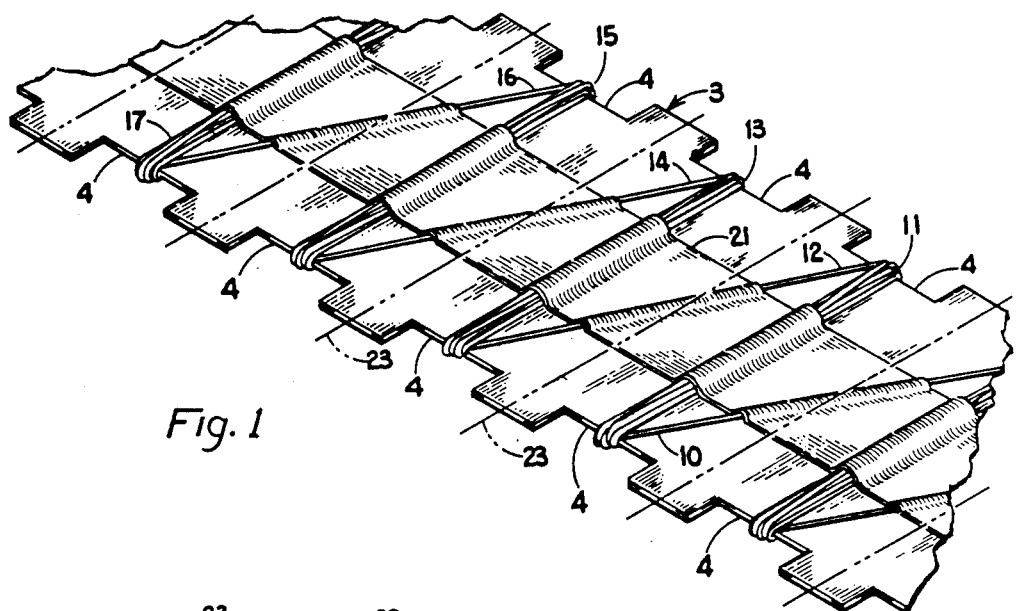
FIG. 1 is a perspective fragmentary view illustrating dental floss spindles according to the invention in the process of their production.

Referring now to the drawings and particularly to FIG. 1, there is shown an elongated strip of semi-rigid sheet material 3 from which spindles according to the invention are produced. For purposes of explanation "sheet material" will be considered to be of uniform thickness from about 0.01 inch to about 0.1 inch. The sheet material 3 may be formed of plastic or paperboard, or a combination thereof, and a particular material identified as 0.02" thickness polyvinylchloride manufactured by Klockner Tenta-Plastic of America is suitable raw material for strip 3. As used herein "semi-rigid" means a rigidity comparable to a credit card or playing card.

Strip 3 is provided with rectangular indentations 4, approximately three-eighths inch wide by one-eighths inch deep, and the indentations are spaced apart center to center by five-eighths inch. It will be understood that the dimensions given are exemplary only and are not critical. The dimensions can be varied over a considerable range as may be desired for particular purposes. It is desirable however, that the dimensions be uniform once they are selected, preferably to within 0.005 inches. In FIG. 1 the outside width dimension of strip 3 is one and three-eighths inches.

As shown in FIG. 1 strip 3 has been wound with a series of windings of dental floss identified in FIG. 1 as windings 11, 13, 15 and 17; these windings are part of a continuous strand connected from one to another by sections of dental floss 12, 14, and 16 as shown in FIG. 1.

As to the exact mechanism for producing the dental floss windings 11, 13, and 15 on strip 3 there are numerous options including winding by hand, winding by machine, or some combination thereof. If windings 11, 13, 15, 17, etc. are to be produced by hand, then the strip 3 would preferably be at least ten inches long and up to about thirty inches long, yielding from about sixteen to about forty-eight windings on a strip. A machine winding process might also use such a relatively short length of sheet material for a strip 3, but there would also be a preferred option of using a roll of several hundred feet of strip 3 which could be provided with indentations 4 by a punching operation as it was fed off a large roll just preceding the winding operation. Many other options are available for mechanical apparatus to produce the spindles according to the present invention, but such apparatus forms no part of the present invention, and will not be described in view of the feasibility of producing the spindles according to the invention by hand.

Production of windings 11, 13, 15, and 17 may proceed as follows. Some first winding not shown in FIG. 1 will serve to anchor the end of the dental floss, and in most cases the spindle containing such winding will be non-uniform and will be discarded. The dental floss will be led from the winding immediately preceding (to the right of) winding 11 as shown at 10. Winding 11 may be formed by making thirteen complete revolutions counterclockwise of the bight of the dental floss to place approximately eighteen inches of floss on winding 11. The bight of the floss is led obliquely as shown at 12 to the starting point of the following winding 13 which may likewise be formed by thirteen revolutions of the floss, the last of which forms a transition strand 14 leading to winding 15 and so on.

The preferred method of winding is to rotate the bight of the floss from stock from a spool or the like around the strip 3, but it will be apparent that the strip 3 could be rotated rather than the floss or even that both could be rotated to achieve essentially the same winding effect.

A self-adhesive tape 21 is applied over the windings and transition strands 10–17 as a convenient means of preventing unwinding of the dental floss and subsequent handling, or until the user removes the tape and unwinds the floss just prior to its use.

Self-adhesive tape 21 may consist of any of a number of conventional and readily available self-adhesive tapes formed of plastic film with an adhesive coating, for example, Tape Prod. No. 600 self-adhesive tape manufactured by Minnesota Mining & Mfg. Co. The dental floss utilized is subject to variation, but it is preferably unwaxed dental floss, such as floss labeled floss size 630, made and sold by Odanto Corp., Morrisburg, Ontario, Canada. Of course the invention is not limited to unwaxed dental floss and may be applied to waxed dental floss, flavored dental floss, medication or dentifrice treated dental floss, or the like.

Self-adhesive tape 21 is most conveniently applied in a strip substantially as long as the strip 3 of semi-rigid sheet material, but self-adhesive tape 21 could be applied in shorter lengths should there by any reason for such procedure. Clearly the tape 21 can only be applied after there are windings such as 11, 13, 15 and 17 for it to be applied over, but the application of tape 21 may commence while additional windings are being produced on a trailing portion of the strip 3.

Figure 2:
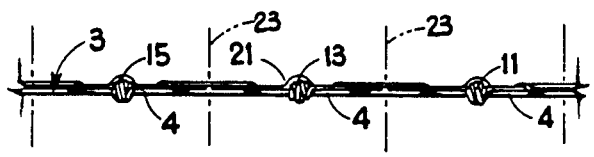
FIG. 2 is an edgewise view of the articles of FIG. 1.
Figure 3:
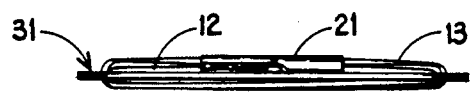
FIG. 3 is an endwise view of the articles of FIG. 1.

Ultimately the strip 3 together with windings 11, 13, 15, and 17, and tape 21 will be severed into individual spindles along phantom lines indicated at 23 in FIGS. 1 and 2. Cutting of the strip 3 into individual spindles can proceed at any point after tape 21 is laid down and may proceed while other portions of tape 21 are still being laid down, and while other windings are still being produced on strip 3. FIGS. 2 and 3 show the strip 3 with windings 11, 13, 15, and 17, and tape 21 in place prior to cutting along lines 23, supplementing the showing of FIG. 1.

Figure 4:
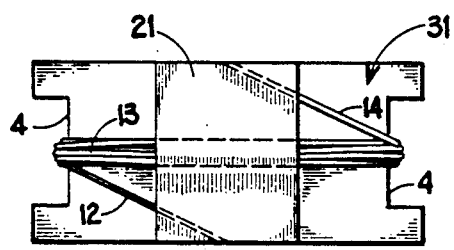
FIG. 4 is a top plan view of a finished single use dental floss spindle produced in the manner shown in FIG. 1.

FIG. 4 shows a finished individual single use dental floss spindle 31 produced by cutting off a segment of strip 3 shown in FIGS. 1, 2, and 3. It will be seen in FIG. 4 that both the beginning end 12 and the finishing end 14 of the dental floss are secured so that the spindle 31 may be handled in bulk in further processing, packaging or transportation without causing the floss to unwind or entangle.

At the same time the floss is readily removed for use by unpeeling self-adhesive tape 21 from spindle 31 and grasping finishing end 14 to allow easy unwinding of the floss from the spindle 31. If desired, the finishing end 14 of the dental floss may be identified by a dot or other mark on the spindle 31 so that the user will not try to unwind from the wrong end, i.e. the beginning end 12 as shown in FIG. 4. However, such marking is generally thought unnecessary because the proper end 14 becomes readily identifiable as it will fall away from the spindle 31 once tape 21 has been removed (or if the spindle is bent). On the other hand, beginning strand end 12 tends to be captured by overlaid strands of winding 13.

Figure 5:
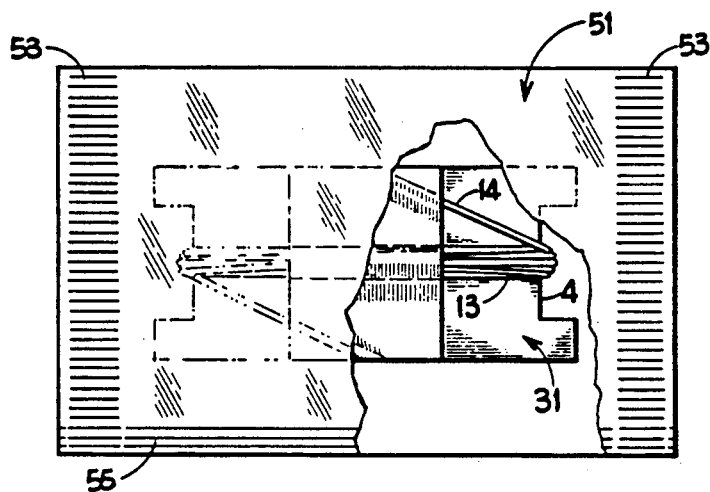
FIG. 5 is a top plan view partially broken away showing a sealed package containing a dental floss spindle as shown in FIG. 4.

In many instances it will be desirable to provide dental floss spindles such as 31 in sealed sanitized packages as shown in FIG. 5. Various forms of conventional machines are readily available for packaging such small articles in individual bags or envelopes, and it is contemplated that such packaging would be accomplished by machine rather than by hand, although hand sealing of the packages is possible with simple heat sealing equipment.

An exemplary package 51 shown in FIG. 5 includes the enclosed spindle 31 with substantially airtight seals 53 on the ends, and a further airtight seal 55 on the edge of the folded plastic material comprising package 51. Package 51 is shown formed of transparent plastic material, but opaque or translucent material could also be used for the package. Sanitization or sterilization of the package may be accomplished by heating or radiating with gamma radiation in accordance with customary practices in the packaging art.

As is well known in the packaging art, the envelope 51 may be arranged to be readily torn for opening or a tear strip may be provided to facilitate opening.

Figure 6:
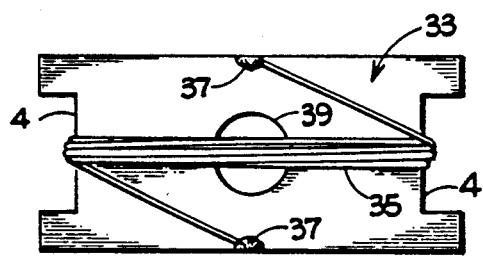
FIG. 6 is a top plan view of an alternative form of dental floss spindle according to the invention.

FIG. 6 shows an alternative form of spindle 33 which may be produced according to the invention. Spindle 33 has indentations 4 similar to those previously described for spindle 31 and also includes a circular opening 39 not provided in spindle 31. Such an opening 39 may be produced in a strip such as strip 3 of FIG. 1 in conjunction with the indentations 4 by cutting or punching machines of conventional form.

Circular opening 39 may be useful in stepping the strips such as strip 3 in FIG. 1 for punching and also for winding; opening 39 also may facilitate detection of some malfunction causing the floss 35 to be broken or improperly wound.

Spindle 33 also differs in that small dots of non-toxic gum-like adhesive material 37 such as used on gummed tape, stamps, etc. are utilized to hold the ends of the floss winding 35 in place. Thus the process for producing the spindle of FIG. 6 would omit the step of laying down tape 21 and in its place dots 37 would be deposited on the strip 3 midway between successive ones of the windings. The subsequent cutting operation would cut through dots 37 and the dental floss to separate successive spindles while securing the dental floss ends to the spindle edges.

Figure 7:
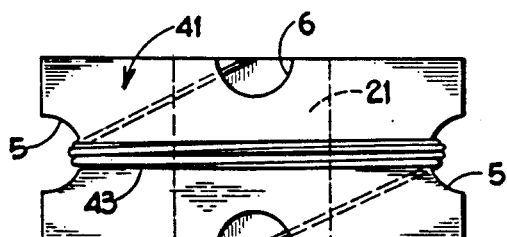
FIG. 7 is a top plan view of a second alternative form of dental floss spindle according to the invention.

FIG. 7 shows another alternative form of spindle that may be produced according to the invention. Spindle 41 is shown from the bottom side with tape 21 positioned on the back side as shown by dashed lines.

Spindle 41 has semi-circular indentations 5 in the place of rectangular indentations as shown in FIGS. 1 through 6. There are additional semi-circular indentations 6 in the long sides of the spindle 41. It will be noted that semi-circular indentations 6 of FIG. 7 started as circular openings in a strip such as strip 3 of FIG. 1. Thus the starting strip to form spindles 41 of FIG. 7 would have centrally positioned circular openings similar to open 39 in spindle 33 of FIG. 6 except that the openings would be staggered with respect to the indentations 5 rather than being aligned with them. Indentations 6 may perform an indexing function and also serve to facilitate removal of the tape 21 which is exposed and readily grasped within the openings 6.

Figure 8:
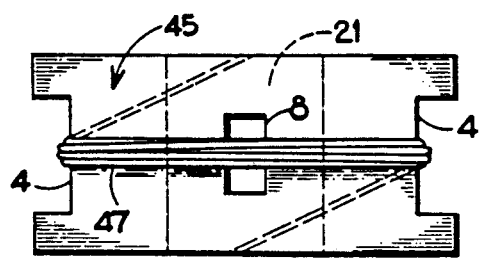
FIG. 8 is a top plan view of a third alternative form of dental floss spindle according to the invention.

FIG. 8 shows a still further alternative form of spindle 45 which may be produced according to the invention. Spindle 45 differs from the previously illustrated spindles in that there is a central opening 8 which is rectangular rather than circular as in the case of the opening 39 in FIG. 6. The rectangular opening 8 may in some cases provide better control of the positioning of the winding 47 on spindle 45.

It will be apparent to those skilled in the art that numerous other variations may be made to the spindle configurations in addition to those shown in FIGS. 1-5, 6, 7, and 8. For example, indentations 6 on the side shown in FIG. 7 could also be utilized with other embodiments and in general the specific features shown may be combined in numerous different ways. In the preferred embodiments shown, circular or semi-circular openings are one-quarter inch in diameter, and the rectangular indentations are three-eighths inch by one-eighths inch while the rectangular center opening 8 of FIG. 8 is one-eighth inch by one-quarter inch. The tape is one-half inch wide. Clearly all of these dimensions are exemplary only, and are subject to wide variation. A common feature of all embodiments is that at least some indentations or openings are formed in the strip of semi-rigid material before the winding process is carried out.

While it is theoretically possible to wind the dental floss in separated windings on the elongated strip without any indentations or openings whatsoever in the strip, such procedure appears to be impractical. It will be noted that FIGS. 1-5 show a spindle with indentations, but without other openings as a practical embodiment and, although not shown, an embodiment similar to FIG. 7 without indentations 5 also appears to be feasible. At present the most preferred embodiment appears to be FIG. 7 as shown.

In addition to the variations and modifications to the invention which have been shown, described or suggested above, other variations and modifications will be apparent to those skilled in the art, and accordingly the scope of the invention is not to be considered to be limited to those variations of the invention shown or suggested, but is rather to be determined by reference to the appended claims.

What is claimed is:

1. Spindles holding a single use length of dental floss in the form of a generally rectangular sheet of semi-rigid material less than three inches long and less than one inch wide having about one to three feet of dental floss removably secured thereon produced by the process steps of
  (a) winding from about 6 to about 30 turns of dental floss transversely at a winding position on a semi-rigid elongated strip of sheet material greater than ten inches long and less than three inches wide,
  (b) then leading dental floss from the immediate previous winding position extending along a front face of said sheet material obliquely from one lateral edge of said strip at the immediate previous winding position to the opposite lateral edge at another winding position longitudinally at least one-fourth inch past the immediate previous winding position and winding from about 6 to about 30 turns of dental floss transversely on said strip at said another position,
  (c) repeating step (b) at least five times,
  (d) subsequent to step (b) removably adhering a portion of an elongated narrow pressure sensitive tape longitudinally over the front face of said sheet material and at least one dental floss winding thereon,
  (e) repeating step (d) at least five times,
  (f) subsequent to step (d) transversely cutting said elongated strip of sheet material, said dental floss and said web along a transverse line midway between successive ones of said winding positions,
  (g) repeating step (f) at least five times to produce at least one of said spindles,
  (h) sealing each spindle produced in an air-tight envelope, and
  (i) sterilizing the spindle, floss and interior of said envelope.

2. Spindles as recited in claim 1 wherein each said winding position is marked by an indentation in at least one edge of said elongated strip of sheet material.

3. Spindles as recited in claim 1 wherein each said indentation is rectangular in shape.

4. Spindles as recited in claim 1 wherein each said indentation is semi-circular in shape.

5. Spindles holding a single use length of dental floss in the form of a generally rectangular sheet of semi-rigid material having about one foot to about three feet of dental floss removably secured thereon produced by the process steps of
  (a) winding from about 6 to about 30 turns of dental floss transversely at a winding position on a semi-rigid elongated strip of sheet material,
  (b) then leading dental floss from the immediate previous winding position extending along a front face of said sheet material obliquely from one lateral edge of said strip at the immediate previous winding position to the opposite lateral edge at another winding position longitudinally at least one-fourth inch from the immediate previous winding position and winding from about 6 to about 30 turns of dental floss transversely on said strip at the last said another winding position,
  (c) repeating step (b) at least once,
  (d) subsequent to step (b) removably securing at least a portion of an elongated web longitudinally over the front face of said sheet material and at least one dental floss winding thereon,
  (e) repeating step (d) at least once,
  (f) subsequent to step (d) severing said elongated strip of sheet material, said dental floss and said web along a transverse line between successive ones of said winding positions,
  (g) repeating step (f) at least once to produce at least one of said spindles.

6. Spindles as recited in claim 5 wherein each said winding position is marked by an indentation in at least one edge of said elongated strip of sheet material.

7. Spindles as recited in claim 5 wherein the step of winding dental floss as recited in step (a) or step (b) is accomplished by rotating a bight of said dental floss around said elongated strip.

8. Spindles as recited in claim 5 wherein said elongated web is a pressure sensitive adhesive tape from about one-quarter inch to about three-quarters inch in width and is placed along the longitudinal mid-line of said elongated strip of sheet material.

9. A spindle holding a single use length of dental floss in the form of a generally flat sheet having at least about one foot of dental floss wound thereon produced by the process steps of
  (a) winding at least about 6 turns of dental floss transversely at a winding position on an elongated strip of sheet material,
  (b) leading dental floss from a previous winding position along a face of said sheet material from one lateral edge of said strip at said previous winding position to the opposite lateral edge at another winding position and winding at least about 6 turns of dental floss transversely on said strip at said another winding position,
  (c) repeating step (b) at least once,
  (d) subsequent to step (b) securing at least a portion of the dental floss lead from one to another of said winding positions on a face of said sheet material,
  (e) repeating step (d) at least once,
  (f) subsequent to step (d) severing said elongated strip of sheet material, and said dental floss between successive ones of said winding positions,
  (g) repeating step (f) at least once to produce at least one of said spindles.

10. A spindle as recited in claim 9 wherein each said winding position is marked by an indentation in at least one edge of said elongated strip of sheet material.

11. A spindle as recited in claim 10 wherein said indentations are spaced longitudinally at a distance from one-half inch to three-quarters inch center to center.

12. A spindle as recited in claim 10 wherein each said indentation is rectangular in shape.

13. A spindle as recited in claim 10 wherein each said indentation is semi-circular in shape.

14. A spindle as recited in claim 9 wherein the step of winding dental floss as recited in step (a) or step (b) is accomplished by rotating a bight of said dental floss around said elongated strip.

15. A spindle as recited in claim 9 wherein said dental floss is secured on a face of said sheet material by application of pressure sensitive adhesive tape from about one-quarter inch to about three-quarters inch in width along the longitudinal mid-line of said elongated strip of sheet material.

16. Single-use dental floss spindle produced from a strip of sheet material having a plurality of indentations punched along the edge thereof, by process steps of
  (a) winding a strand of dental floss at the middle of a spindle position at least twice around the indentations of the first spindle position of said strip,
  (b) advancing the strip so that the floss is laid across the face of the spindle to the middle of a second spindle position, (c) taping the floss to the strip with pressure sensitive adhesive tape which runs perpendicular to the winding,
(d) severing a finished spindle and floss from the card,
(e) repeating the previous steps to produce additional spindles.

17. A method for producing spindles holding a single-use length of dental floss in the form of a generally flat sheet of material having dental floss wound thereon comprising the steps of
    (a) winding at least about 6 turns of dental floss from a continuous strand at least 10 feet long transversely at a winding position on an elongated strip of sheet material,
    (b) leading dental floss from a previous winding position along a face of said sheet material from one lateral edge of said strip at said immediate previous winding position to the opposite lateral edge at another winding position and winding at least about 6 turns of dental floss transversely on said strip at the last said another winding position,
    (c) repeating step (b) at least once,
    (d) subsequent to step (b) removably securing at least a portion of the dental floss extending between winding positions to the face of said sheet material,
    (e) repeating step (d) at least once,
    (f) subsequent to step (d) severing said elongated strip of sheet material, said dental floss and said web between successive ones of said winding positions,
    (g) repeating step (f) at least once to produce at least one of said spindles.

18. The method recited in claim 17 further including sealing each spindle in an air tight envelope and sterilizing the spindle and interior of said envelope.

19. A method for producing spindles holding a single-use length of dental floss in the form of a sheet of material having dental floss wound thereon comprising the steps of
    (a) winding about 6 to about 30 turns of dental floss from a continuous strand at least 10 feet long transversely at a winding position on an elongated strip of sheet material,
    (b) then leading dental floss from the immediate previous winding position extending along a front face of said sheet material obliquely from one lateral edge of said strip at the immediate previous winding position to the opposite lateral edge at another winding position longitudinally at least one-quarter inch from the immediate previous winding position and winding from about 6 to about 30 turns of dental floss transversely on said strip at the last said another winding position,
    (c) repeating step (b) at least once,
    (d) subsequent to step (b) removably securing at least a portion of an elongated narrow web longitudinally over the front face of said sheet material and dental floss windings thereon,
    (e) repeating step (d) at least once,
    (f) subsequent to step (d) severing said elongated strip of sheet material, said dental floss and said web along a transverse line between successive ones of said winding positions,
    (g) repeating step (f) at least once to produce at least one of said spindles.

20. The method recited in claim 19 further including sealing each spindle in an air tight envelope and sterilizing the spindle, the floss and the interior of said envelope.

* * * * *